(12) United States Patent
Migita

(10) Patent No.: US 6,923,766 B2
(45) Date of Patent: Aug. 2, 2005

(54) ULTRASONIC DIAGNOSTIC APPARATUS AND ULTRASONIC DIAGNOSTIC METHOD

(75) Inventor: Manabu Migita, Neyagawa (JP)

(73) Assignee: Matsushita Electric Industrial Co., LTD, Osaka (JP)

( * ) Notice: Subject to any disclaimer, the term of this patent is extended or adjusted under 35 U.S.C. 154(b) by 0 days.

(21) Appl. No.: 10/682,931

(22) Filed: Oct. 14, 2003

(65) Prior Publication Data

US 2004/0077947 A1 Apr. 22, 2004

(30) Foreign Application Priority Data

Oct. 15, 2002 (JP) ...................................... 2002-300957

(51) Int. Cl.[7] .............................................. A61B 8/00
(52) U.S. Cl. ..................................................... 600/443
(58) Field of Search ................................ 600/442, 443, 600/447, 454–456, 458; 73/625–626

(56) References Cited

U.S. PATENT DOCUMENTS

| | | | |
|---|---|---|---|
| 5,235,985 A | | 8/1993 | McMorrow et al. |
| 5,526,816 A | * | 6/1996 | Arditi ........................... 600/458 |
| 5,833,614 A | * | 11/1998 | Dodd et al. .................. 600/447 |
| 5,913,823 A | * | 6/1999 | Hedberg et al. ............. 600/443 |
| 5,961,460 A | * | 10/1999 | Guracar et al. ............. 600/440 |
| 5,961,464 A | * | 10/1999 | Poland ......................... 600/458 |
| 6,132,377 A | * | 10/2000 | Bolorforosh et al. ........ 600/458 |
| 6,181,810 B1 | | 1/2001 | Zhang et al. |
| 6,193,659 B1 | * | 2/2001 | Ramamurthy et al. ...... 600/443 |
| 6,221,018 B1 | | 4/2001 | Ramamurthy et al. |

FOREIGN PATENT DOCUMENTS

JP 5-80217 11/1993

* cited by examiner

*Primary Examiner*—Francis J. Jaworski
(74) *Attorney, Agent, or Firm*—Wenderoth, Lind & Ponack, L.L.P.

(57) ABSTRACT

A beam forming and adding unit receives an echo signal containing reflection by a side lobe of an ultrasonic pulse, and executes its focusing. A fundamental wave BPF unit and a fundamental wave detecting unit extract a fundamental wave component from the echo signal, and calculate its signal power. A harmonics BPF unit and a harmonics detecting unit extract a harmonics component from the echo signal, and calculate its signal power. A ratio calculating unit and a ratio comparing unit calculate a ratio of these two calculated signal powers, compare this power ratio with a power ratio threshold value stored in a reference memory, and notify its comparison result to a detection signal suppressing unit. The detection signal suppressing unit suppresses the echo signal according to the notification result, and outputs the echo signal. A display unit generates and displays an ultrasonic image based on the output echo signal.

20 Claims, 12 Drawing Sheets

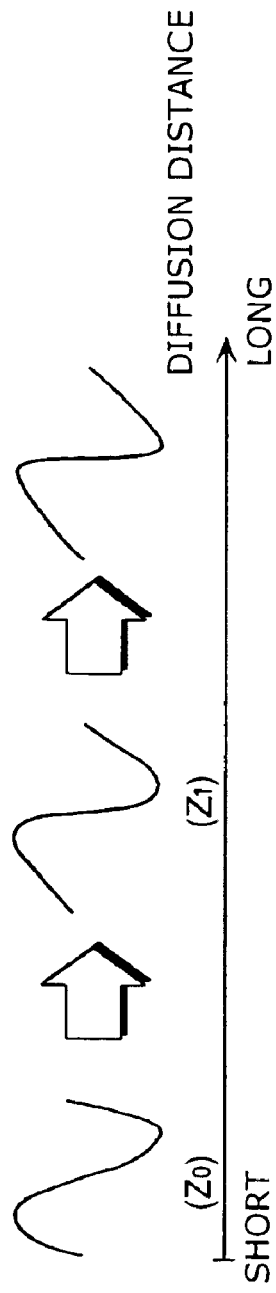
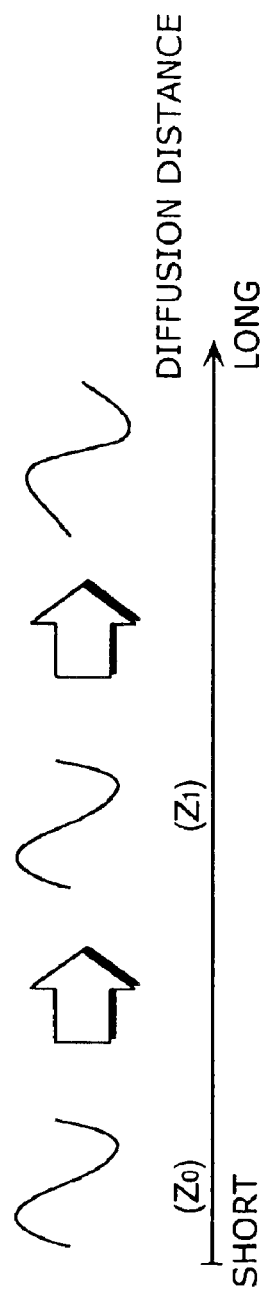
Fig. 6A WAVEFORM OF RECEIVED DETECTION SIGNAL WHEN POWER OF ULTRASONIC PULSE SENT IS BIG (IN THE CASE OF MAIN LOBE)
Fig. 6B WAVEFORM OF RECEIVED DETECTION SIGNAL WHEN POWER OF ULTRASONIC PULSE SENT IS SMALL (IN THE CASE OF SIDE LOBE)

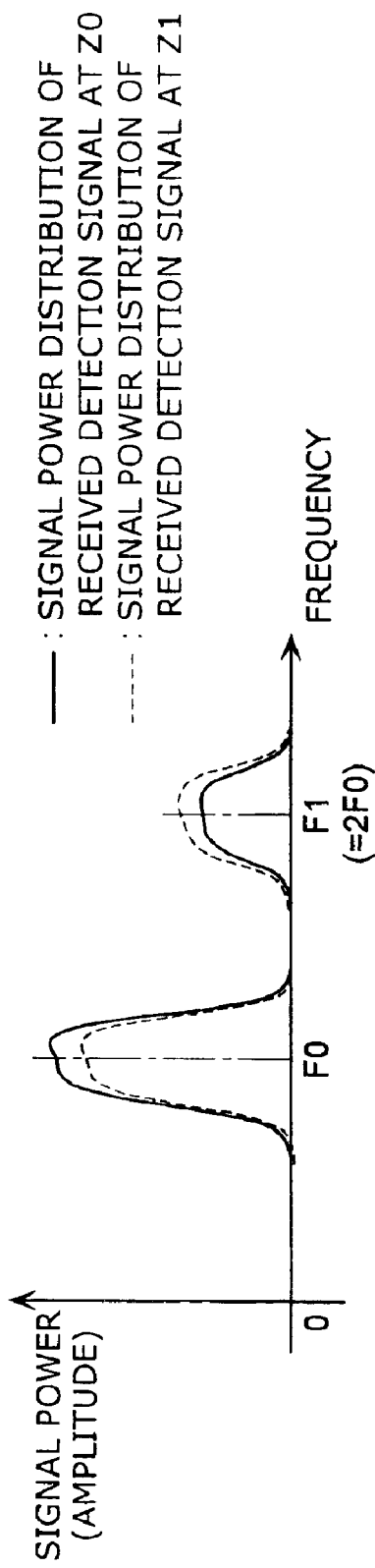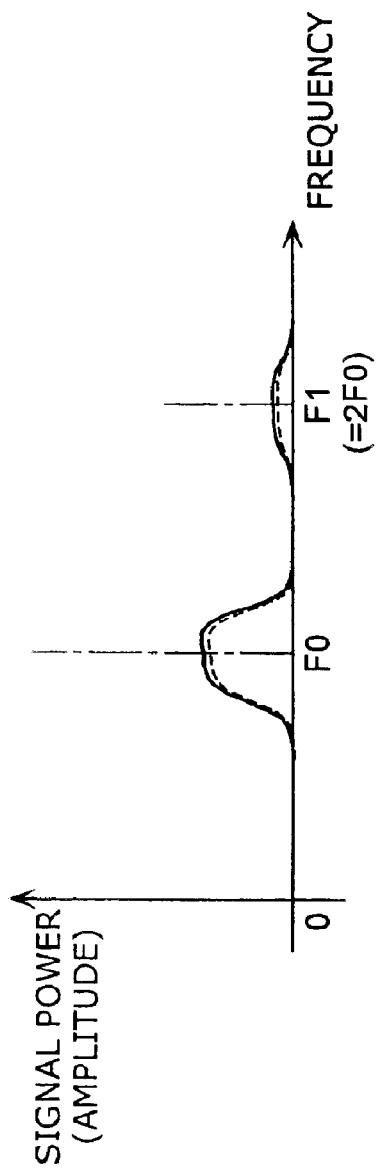

ULTRASONIC DIAGNOSTIC APPARATUS AND ULTRASONIC DIAGNOSTIC METHOD

BACKGROUND OF THE INVENTION (1) Field of the Invention

The present invention relates to an ultrasonic diagnostic apparatus, and especially relates to a technology for reducing an artifact (a virtual image) which is contained in an ultrasound image.

(2) Description of the Related Art

An ultrasonic diagnostic apparatus, which enables observing an object to be tested in a noninvasive and real time manner, has had an irreplaceable existence in the medical field. The ultrasonic diagnostic apparatus is an apparatus which sends an ultrasonic pulse that is generated by a probe (a search unit) to the object, and visualizes a condition in the object into an image according to a reflected ultrasonic echo. (For example, see pp 7–20 and pp 24–25 in "Ultrasonic Medical Science TEXT Basic Ultrasonic Medical Science" written by Itoh and Hirata in April, 1998 published by Ishiyaku Shuppan Co., Ltd.)

The following explains a configuration of a conventional ultrasonic diagnostic apparatus and the actions which are taken by the conventional ultrasonic diagnostic apparatus.

FIG. 1 is a block diagram that shows a functional configuration of the conventional ultrasonic diagnostic apparatus 70.

As shown in FIG. 1, the conventional ultrasonic diagnostic apparatus 70 is composed of a search unit 71, a send/receive switching unit 72, a sending unit 73, a beam forming and adding unit 74, a filtering unit 75, a detecting unit 76 and a display unit 77.

The search unit 71 is an apparatus that sends an ultrasonic pulse to an object to be examined, and receives an ultrasonic signal (hereinafter referred to as an "ultrasonic echo") that is reflected from the object. When the search unit 71 sends the ultrasonic pulse, the search unit 71 receives a pulse signal (hereinafter referred to as a "transmission pulse signal") to generate the ultrasonic pulse from the sending unit 73, and generates the ultrasonic pulse based on the transmission pulse signal. On the other hand, when the search unit 71 receives the ultrasonic echo, the search unit 71 converts the ultrasonic echo that is reflected from the object into an electric signal (hereinafter referred to as a "received echo signal"), and outputs the electric signal to the send/receive switching unit 72.

When the ultrasonic pulse is sent from the search unit 71, the send/receive switching unit 72 connects the search unit 71 with the sending unit 73. On the other hand, when the ultrasonic pulse is received, the send/receive switching unit 72 switches the search unit 71 to connect with the sending unit 73. When the ultrasonic pulse is sent, the sending unit 73 generates the transmission pulse signal, and outputs the transmission pulse signal to the send/receive switching unit 72.

The beam forming and adding unit 74 executes focusing and all necessary beam formation and addition to the received echo signal that is received from the search unit 71 via the send/receive switching unit 72, and outputs the received echo signal to the filtering unit 75. The filtering unit 75 executes a filtering process to the received echo signal that is output from the beam forming and adding unit 74. The detecting unit 76 executes envelope detection to the received echo signal, which has been processed through the filtering process and outputted from the filtering unit 75, and outputs the received echo signal after the detection process (hereinafter referred to as a "received detection signal") to the display unit 77. The display unit 77 generates an ultrasonic image based on the received detection signal that is output from the detecting unit 76.

Actions which are taken in the conventional ultrasonic diagnostic apparatus 70 will now be explained. For sending the ultrasonic pulse to the object, the transmission pulse signal is generated in the sending unit 73. The ultrasonic pulse which is generated based on this transmission pulse signal is sent to the object from the search unit 71. The ultrasonic pulse which is sent to the object is reflected at a sound impedance boundary within the object, and comes back to the search unit 71 with a time delay that is caused according to a reflection depth after the transmission has been started. The search unit 71 converts the received ultrasonic echo into the received electric echo signal, and outputs the received echo signal to the beam forming and adding unit 74. The beam form and adding unit 74 corrects the difference in the receiving time when each of the oscillators composing the search unit 71 receives the ultrasonic echo, and executes focusing on the received echo signal.

In addition, because the received echo signal after the beam formation and addition contains some noise components, a filtering process by a band pass filter (BPF) is executed for efficiently extracting the received echo signal in the harmonics frequency, which is a central frequency or twice of the central frequency in the filtering unit 75. The received echo signal that has been through the filtering unit 75 is multiplexed by using a Hilbert conversion filter in the detecting unit 76. Then, after the received echo signal is multiplexed, by applying the envelope detection to the received echo signal, the echo signal is converted into the received detection signal which shows luminance for generating an ultrasonic image, and the like. Lastly, the display unit 77 receives the detection signal from the detecting unit 76, generates the ultrasonic image based on the received detection signal, and displays the generated ultrasonic image on a display apparatus, or the like.

For the ultrasonic diagnostic apparatus, an ultrasonic pulse having a desired directivity (for example, a feature to have a stronger acoustic pressure in a front direction) is used for improving the picture quality of the ultrasonic image.

However, the ultrasonic pulse which is actually sent contains a plural number of side lobes that are sent in an undesired direction (for example, 45 degrees in both right and left directions) in addition to the main lobe that is sent in a desired direction (in the front direction).

FIG. 2 is a diagram that shows an overview of a plural number of side lobes 82 and 83, which are generated at both sides of a main lobe 81 and sent in undesired directions (i.e. In right and left oblique directions; hereinafter, such undesired directions are referred to as a "side lobe direction"). Because of these side lobes, the side lobe of the ultrasonic pulse is sent to an object which is located in the side lobe direction. When the ultrasonic diagnostic apparatus 70 receives the ultrasonic echo, the ultrasonic diagnostic apparatus 70 receives the ultrasonic echo that is reflected from the object which is located in the side lobe direction at the same time the ultrasonic diagnostic apparatus 70 also receives the main lobe of the ultrasonic pulse that is reflected from the object which can reflect the ultrasound to be displayed as the ultrasound image. As a result, the ultrasonic echo that is reflected from the object which is located in the side lobe direction is generated as an artifact (a virtual image), and causes a problem to induce misdiagnosis through the ultrasound image containing the artifact (Please see the aforementioned reference book).

FIG. 3 is a pattern diagram showing a process in which the artifact (a virtual image) that is generated by the above-described side lobes 82 and 83 are displayed as the ultrasound image. As shown in FIG. 3, there are objects 91 and 92 that can reflect an ultrasound to be displayed as the ultrasound image, the main lobe of the ultrasonic pulse is reflected from these objects, and the received echo signals 96 and 97 are generated. However, this ultrasonic pulse contains the side lobe. When there are objects 93–95 which are located in both the right and left side lobe directions, which objects are not desired to be displayed as the ultrasound image and from which the ultrasound may be reflected, these objects reflect the side lobe so that the received echo signals 93a–95a are generated. As a result, the signals 93a–95a through the above-described side lobe remain even in the received detection signal, and these appear as the artifact.

SUMMARY OF THE INVENTION

In view of the above-described issues and problems, an object of the present invention is to provide an ultrasonic diagnostic apparatus and an ultrasonic diagnostic method for preventing any wrong diagnosis due to an artifact (a virtual image) which is caused by a side lobe.

In order to achieve the above-described object, the ultrasonic diagnostic apparatus may be an ultrasonic diagnostic apparatus that generates and displays an ultrasonic image of an object to be examined based on a reflection of an ultrasound having a main lobe and a side lobe. The ultrasonic diagnostic apparatus comprises: an ultrasonic sending/receiving unit operable to generate the ultrasound, receive the ultrasound that is reflected from the object, and convert the ultrasound into an electric signal; a first calculating unit operable to extract a fundamental wave frequency component from the converted electric signal and to calculate power of the signal; a second calculating unit operable to extract a harmonics frequency component from the converted electric signal and to calculate the power of the signal; a power ratio calculating unit operable to calculate a ratio of the calculated power of the signal of the fundamental frequency component to the calculated power of the signal of the harmonics frequency component; an output controlling unit operable to control and output the electric signal of the fundamental wave frequency component based on a value of the calculated ratio; and an image display unit operable to generate and display an ultrasonic image based on the output electric signal.

Additionally, to achieve the above-described object, the ultrasonic diagnostic apparatus related to the present invention is an ultrasonic diagnostic apparatus that generates and displays a ultrasonic image of an object to be examined based on a reflection of an ultrasound having a main lobe and a side lobe. The ultrasonic diagnostic apparatus comprises: an ultrasound sending/receiving unit operable to generate the ultrasound, receive the ultrasound that is reflected from the object, and convert the ultrasound into an electric signal; a first calculating unit operable to extract a fundamental wave frequency component from the converted electric signal and to calculate the power of the signal; a second calculating unit operable to extract a harmonics frequency component from the converted electric signal and to calculate the power of the signal; a power ratio calculating unit operable to calculate a ratio of the calculated power of the signal of the fundamental frequency component to the calculated power of the signal of the harmonics frequency component; an output controlling unit operable to control and output the electric signal of the harmonics frequency component based on a value of the calculated ratio; and an image display unit operable to generate and display an ultrasonic image based on the output electric signal.

Furthermore, to accomplish the above-described object, the present invention may be embodied as a method having characteristic and structural means of the above-described ultrasonic diagnostic apparatus as steps, and may also be embodied as an executable program containing all of these steps. Then, the program is not only be stored in a ROM and the like that are contained in the ultrasonic diagnostic apparatus, but the program may also be distributed through a recording media such as a CD-ROM or a transmission media such as a communication network.

As mentioned above, the ultrasonic diagnostic apparatus according to the present invention decides whether or not the received detection signal is a signal to generate the artifact, by using a difference between the transmission power in the main lobe direction and the transmission power in the side lobe direction within the ultrasonic pulse that is sent from the search unit and by using a difference in the degree of the nonlinear diffusion distortion phenomenon which is contained in the object to be examined. Based on this result, the output level of the is received detection signal is suppressed, and the above-described artifact is reduced, of which practical value is high.

Furthermore, because the main lobe direction has a wide spread in a transmission direction, even lateral resolving power can be improved by appropriately setting the power ratio threshold value that is used in the present invention. As a result, it is possible to construct an ultrasonic diagnosis apparatus that can display the ultrasonic image of which the artifact is reduced and lateral resolving power is improved.

BRIEF DESCRIPTION OF THE DRAWINGS

These and other subjects, advantages and features of the present invention will become apparent from the following detailed description when taken in conjunction with the accompanying drawings which illustrate specific embodiments of the present invention.

FIGS. 6A and 6B are drawings that explain signal waveforms that are distorted by a nonlinear diffusion due to a difference in transmission power.

FIGS. 7A and 7B are examples of signal spectra that are distorted by a nonlinear diffusion due to a difference in transmission power.

DETAILED DESCRIPTION OF THE PREFERRED EMBODIMENTS

The following describes the present invention with reference to several embodiments and the drawings.

First Embodiment

Figure 4:
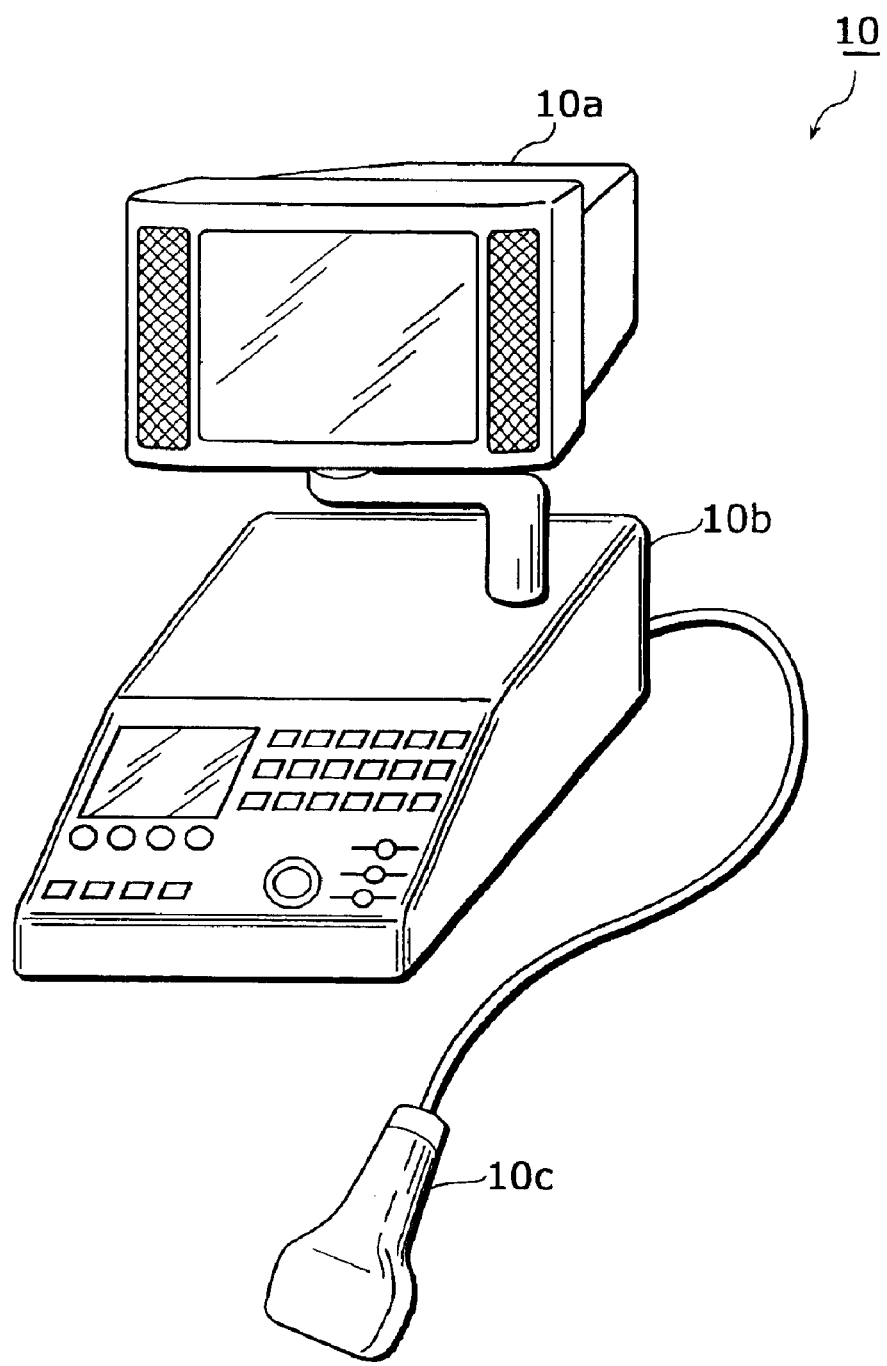
FIG. 4 is an outlook view of the ultrasonic diagnostic apparatus according to a first embodiment of the present invention.

FIG. 4 is an outlook view of the ultrasonic diagnostic apparatus 10 according to the first embodiment. An apparatus 10 is an ultrasonic diagnostic apparatus, which does not just generate an ultrasonic image, but which also reduces an artifact (a virtual image) that is generated by a side lobe and which is capable of providing a more accurate diagnosis. The ultrasonic diagnostic apparatus 10 is mainly composed of a display unit 10a, a main unit 10b and a probe 10c.

The display unit 10a is a display apparatus that is equipped with a liquid crystal display (LCD), a cathode-ray tube (CRT), or the like, which displays an ultrasound image and all necessary information that is obtained through an ultrasonic echo method and the like, and includes a touch panel and the like that accept an input from an operator.

The main unit 10b includes the following elements: a send/receive circuit that controls the transmission/reception of an ultrasound in the probe 10c; a signal/image processing circuit containing a digital signal processor (DSP) and a random access memory (RAM) and the like for processing various types of images and signals; an LCD display containing a group of switches and a mouse as well as a touch panel for receiving the operator's operation; and so on.

The probe 10c is a search unit containing an ultrasonic oscillator, an acoustic lens and the like for receiving and sending the ultrasound.

Figure 5:
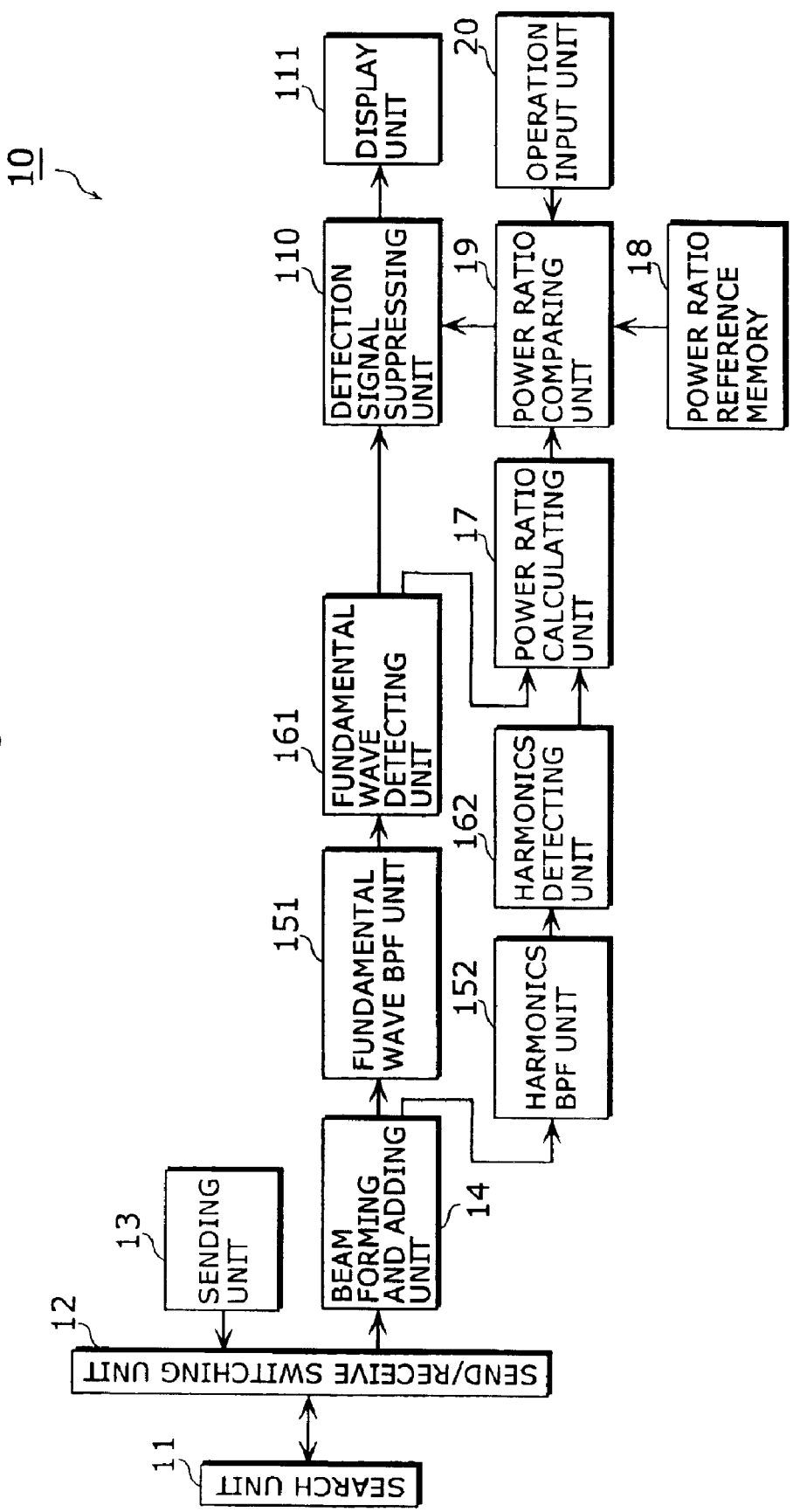
FIG. 5 is a block diagram that shows a functional configuration of the ultrasonic diagnostic apparatus according to the first embodiment.

FIG. 5 is a block diagram that shows a functional configuration of the ultrasonic diagnostic apparatus 10 according to the first embodiment. As shown in FIG. 5, the ultrasonic diagnostic apparatus 10 includes the following elements: a search unit 11; a send/receive switching unit 12; a sending unit 13; a beam forming and adding unit 14; a fundamental wave BPF (band pass filtering) unit 151; a harmonics BPF unit 152; a fundamental wave detecting unit 161; a harmonics detecting unit 162; a power ratio calculating unit 17; a power ratio reference memory 18; a power ratio comparing unit 19; an operation input unit 20; a detection signal suppressing unit 110; and a display unit 111.

The search unit 11 is a unit that generates the ultrasonic pulse and receives the ultrasonic echo that is reflected from the object (equivalent to the probe 10c in the above-described FIG. 4). When the ultrasonic pulse is sent, the search unit 11 generates the ultrasonic pulse based on the transmission pulse signal which is received from the sending unit 13. On the other hand, when the ultrasonic echo is received, the search unit 11 converts the ultrasonic echo that is reflected from the object into a received echo signal, and outputs this received echo signal to the send/receive switching unit 12.

When the ultrasonic pulse is sent, the send/receive switching unit 12 connects the search unit 11 with the sending unit 13. When the ultrasonic pulse is received, the send/receive switching unit 12 switches the search unit 11 to connect with the beam forming and adding unit 14.

When the ultrasonic pulse is sent, the sending unit 13 generates a transmission pulse signal, and outputs the generated transmission pulse signal to the send/receive switching unit 12. The beam forming and adding unit 14 executes focusing for the received echo signal that is received from the search unit 11 via the send/receive switching unit 12, and applies the necessary beam formation and addition.

The fundamental wave BPF unit 151 executes a filtering process to the received echo signal which is output from the beam forming and adding unit 14 for extracting a signal component of a central frequency corresponding to the fundamental wave of the ultrasonic pulse. The harmonics BPF unit 152 executes a filtering process to the received echo signal which is output from the beam forming and adding unit 14 for extracting a signal component of a harmonics frequency composing non-linear distortion which occurred when the fundamental wave of the ultrasonic pulse diffuses in the object.

The fundamental wave detecting unit 161 executes detection to the signal component of the central frequency of the received echo signal which is output from the fundamental wave BPF unit 151. The harmonics detecting unit 162 executes detection to the signal component of the harmonics frequency of the received echo signal which is output from the harmonics BPF unit 152.

The power ratio calculating unit 17 calculates a power ratio in the received detection, signal respectively outputted from the fundamental wave detecting unit 161 and the harmonics detecting unit 162 (for example, a maximum amplitude value of the received detection signal of the harmonics/a maximum amplitude value of the received detection signal of the fundamental wave).

The power ratio reference memory 18 stores a "power ratio threshold value" which is set per diffusion distance (or may be called as a "depth") in the object. "The power ratio threshold value" is a standard value that is used for deciding whether the received detection signal is based on the main lobe or is based on the side lobe. When the power ratio is less than threshold value, the received detection signal is decided to be the received detection signal based on the side lobe. The diffusion distance and the power ratio threshold value are corresponded and memorized. For example, when the spread distance (depth) is "5 cm", the power ratio threshold value is "0.3". When the spread distance (depth) is "10 cm", the power ratio threshold value is "0.35". This power ratio threshold value may be changed by a user via the operation input unit 20.

The power ratio comparing unit 19 compares a "power ratio", which is an output of the power ratio calculating unit 17, with its corresponding "power ratio threshold value" by each diffusion distance (depth), which is stored in the power ratio reference memory 18. The power ratio comparing unit 19 notifies its result (i.e. "it is an artifact", "it is not an artifact" and the like) to the detection signal suppressing unit 110. For example, when the power ratio is "0.1" in the case where the diffusion distance (depth) is "5 cm" and its corresponding power ratio threshold value is "0.3", the power ratio comparing unit 19 decides that the received detection signal is an artifact based on the side lobe.

The detection signal suppressing unit 110 controls the output of the fundamental wave detecting unit 161 based on the notice which is received from the power ratio comparing unit 19. For example, when the detection signal suppressing unit 110 receives a notice that "it is a side lobe" from the power ratio comparing unit 19, the detection signal suppressing unit 110 controls the received detection signal of the fundamental wave. For example, the detection signal suppressing unit 110 reduces the received detection signal of the fundamental wave to 20 percent when outputting it, or does not output it at all.

The display unit 111 generates an ultrasonic image based on the echo signal, which is an output of the detection signal suppressing unit 110, and displays the generated ultrasonic image.

Actions which are taken by the ultrasonic diagnostic apparatus 10 according to the first embodiment will now be explained.

At first, for sending the ultrasonic pulse to the object, the sending unit 13 generates a transmission pulse signal, and sends the transmission pulse signal to the search unit 11. In addition, the search unit 11 generates an ultrasonic pulse based on this transmission pulse signal, and sends the ultrasonic pulse to the object.

In this case, as mentioned in the above-described issues that the invention attempts to resolve, the ultrasonic pulse that is sent from the search unit 11 contains a main lobe and a side lobe. Due to this, the ultrasonic pulse (side lobe) is also sent to an object which is located in the side lobe direction. Therefore, when the ultrasonic diagnostic apparatus 10 receives the ultrasonic echo, the ultrasonic diagnostic apparatus 10 not only receives the ultrasonic echo that is reflected from an object which is desired to be displayed as a diagnostic image which is located in the main lobe direction, but also receives the ultrasonic echo that is reflected from the object which is located in the side lobe direction. As a result, the ultrasonic pulse from the side lobe direction is displayed as an artifact (a virtual image).

Figure 1:
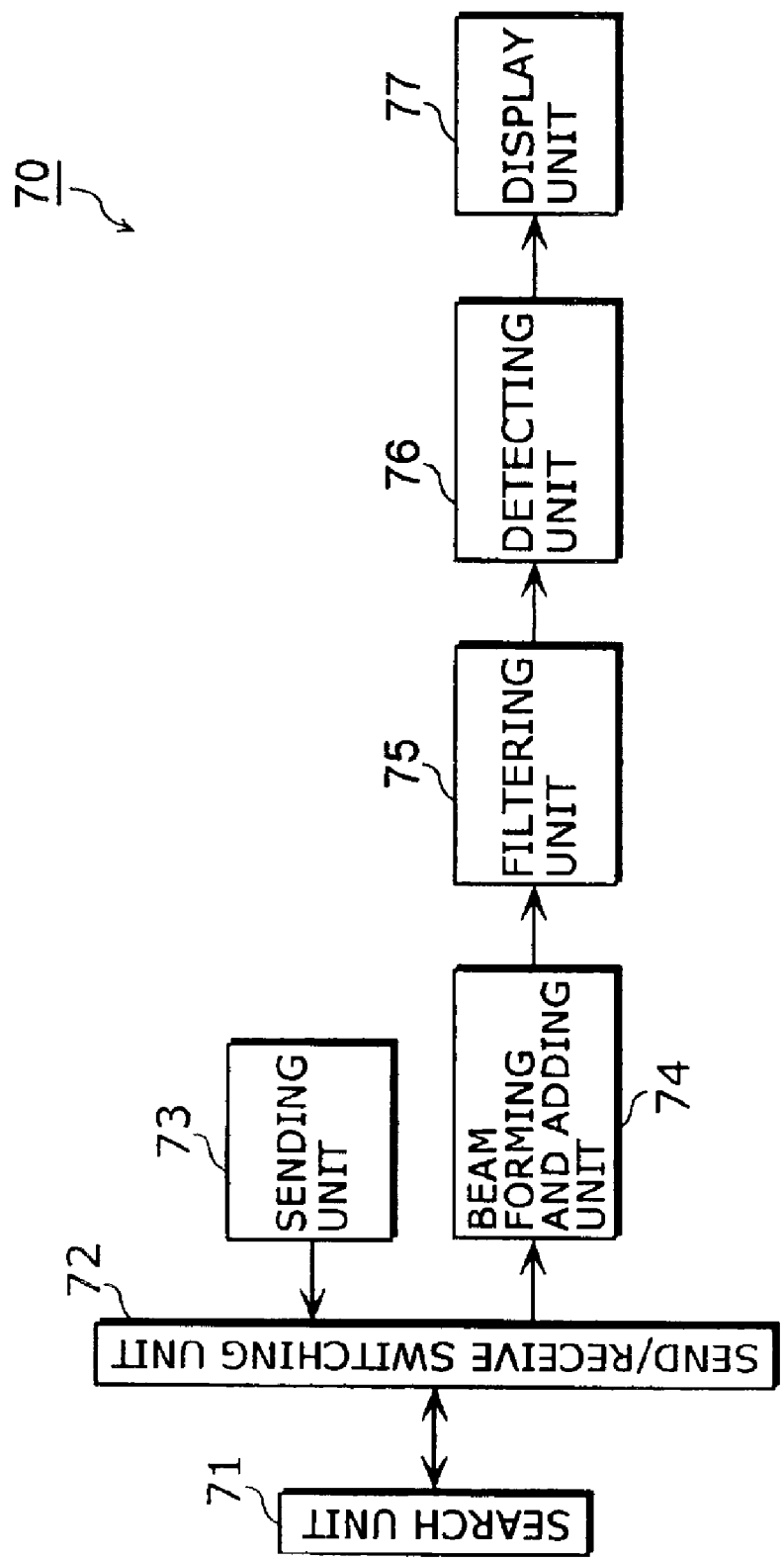
FIG. 1 is an overview diagram that shows a functional configuration of the conventional ultrasonic diagnostic apparatus.
Figure 2:
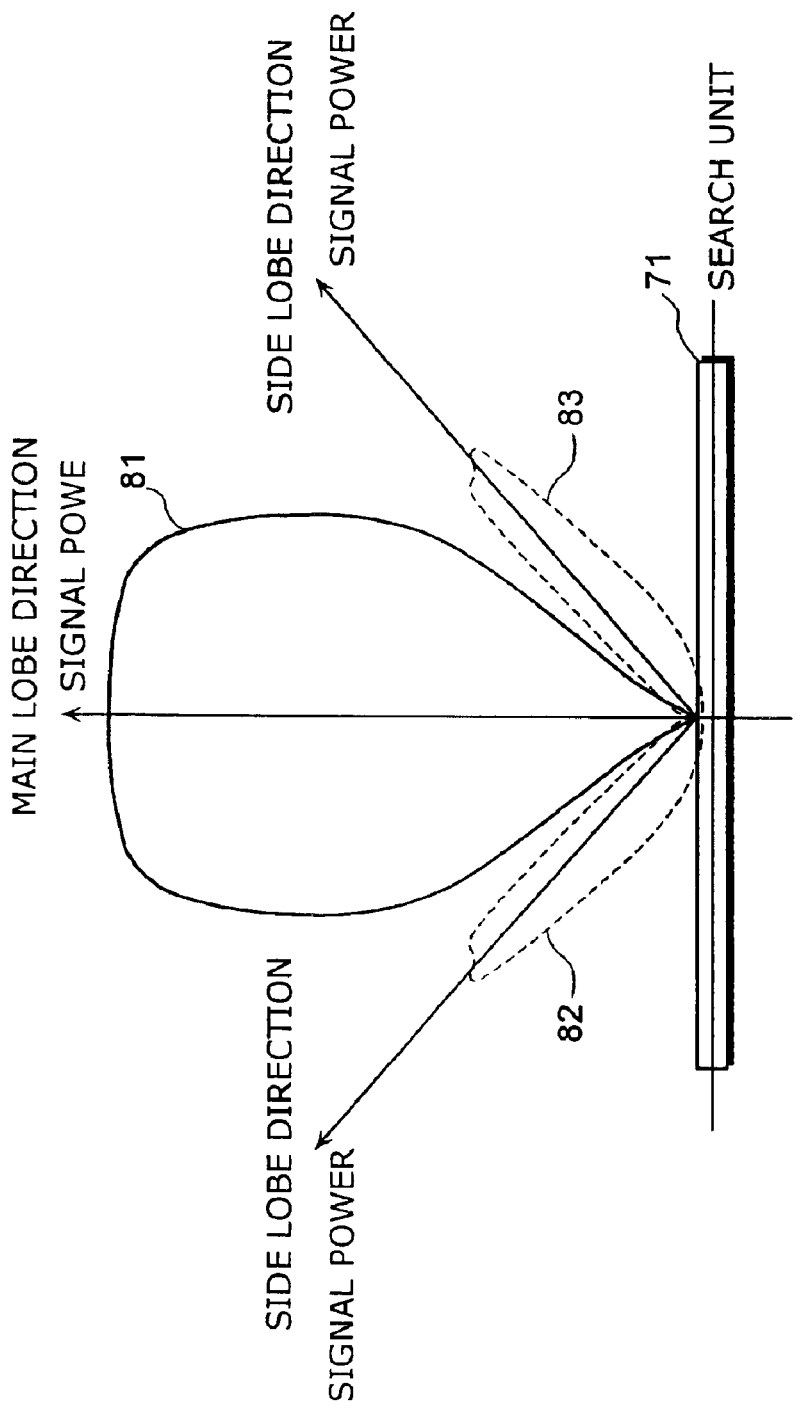
FIG. 2 is a diagram that typically shows the conventional power distribution of the transmission pulse.
Figure 3:
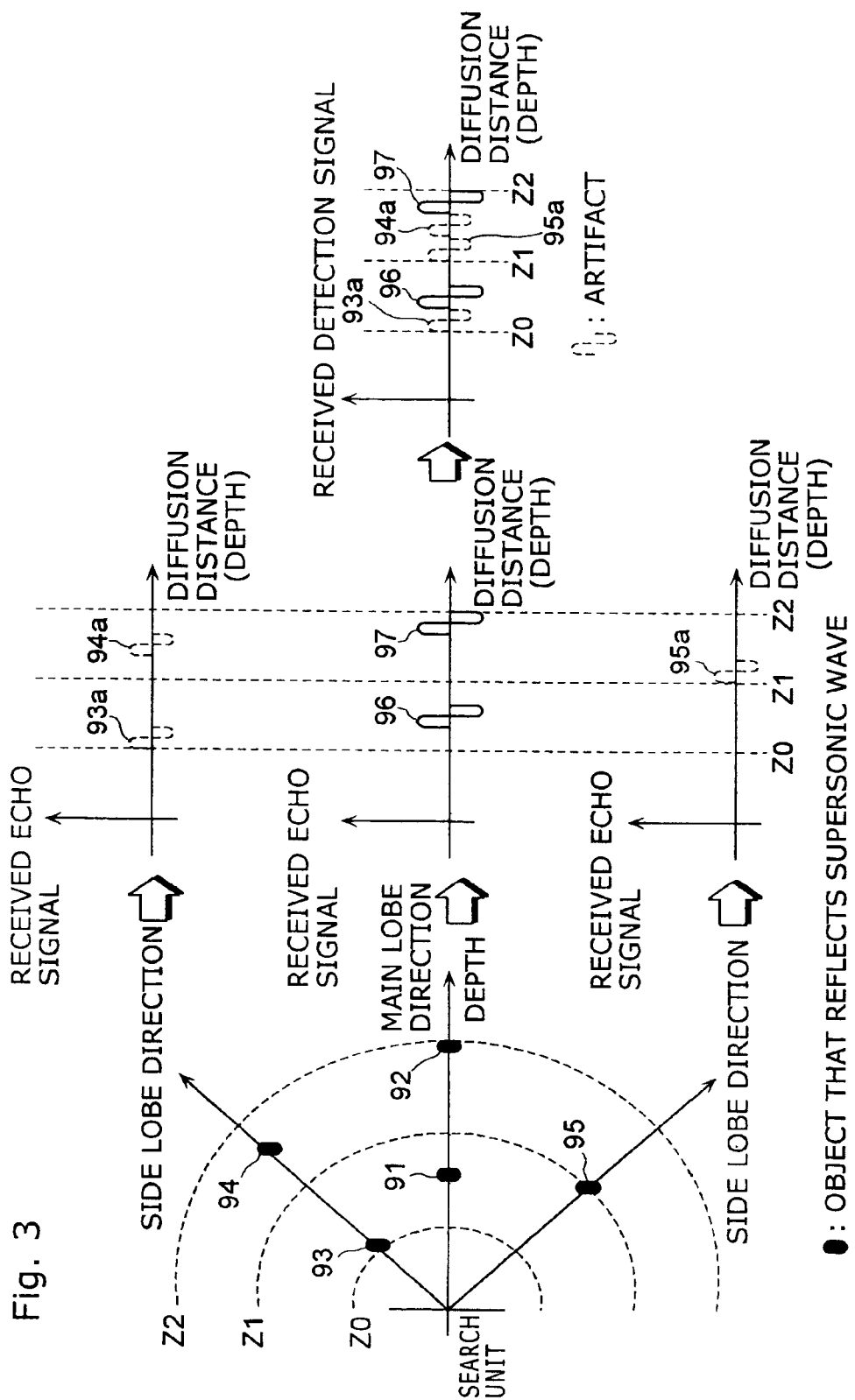
FIG. 3 is a diagram that typically shows the conventional power distribution of the received pulse according to diffusion distance.

There are two remarkable points here. The first point is a difference between the transmission power in the main lobe direction and the transmission power in the side lobe direction within the transmitted ultrasonic pulse. That is to say, as clarified from the above-described FIG. 2, the transmission power in the main lobe direction is bigger (greater) than the transmission power in the side lobe direction. The second point is a phenomenon of nonlinear diffusion distortion which occurs when the ultrasonic pulse goes through the object. This phenomenon is a phenomenon that a wave form of the ultrasonic pulse is gradually distorted as the transmitted ultrasonic pulse diffuses in the object. According to diffusion distance (depth), the ultrasonic pulse has more harmonics frequency components in the transmitted frequency (the fundamental frequency), which is N times (twice, three times, or the like, i.e., N is an integer greater than or equal to two) as much as the one in a regular transmitted frequency (the fundamental wave frequency).

FIG. 6 is a pattern diagram showing the phenomenon of nonlinear diffusion distortion which occurs when the ultrasonic pulse diffuses in the object. FIG. 6A is an example of a wave form of the received echo signal wave in the event that the power of the ultrasonic pulse sent is big (i.e. in the event of the main lobe). FIG. 6B is an example of the received echo signal wave form for a case where the power of the ultrasonic pulse that is sent is small (i.e. in the event of the side lobe). As shown in FIG. 6 (especially FIG. 6A), as the diffusion distance gets longer (the depth gets deeper), the wave form of the received echo signal becomes more saw-toothed. This is because, when the ultrasound goes through a medium (an inside of the object), the ultrasonic pulse moves fast in an area where the power of the ultrasound is big (acoustic pressure is big), and the ultrasonic pulse moves slowly in an area where the power of the ultrasound is small (acoustic pressure is small). Therefore, the wave form becomes saw-toothed, and the distortion as shown in FIG. 6 occurs.

Additionally, as shown in FIG. 6A and FIG. 6B, this phenomenon of nonlinear diffusion distortion is closely related to the power strength, either small or big, of the transmission ultrasonic pulse. For the same reason as above, when the power of the ultrasonic pulse is big, the nonlinear diffusion distortion occurs in a shorter diffusion distance (depth) as compared with a case when the power is small. In other words, when the power is big, big harmonics occur in a shorter diffusion distance (depth).

FIG. 7 is a diagram that typically shows the frequency spectrum of the received detection signal in the nonlinear diffusion distortion phenomenon described above with reference to FIG. 6. FIG. 7A is an example of the frequency spectrum of the received detection signal for a case where the power of the transmission ultrasonic pulse is big (i.e. in the event of the main lobe). FIG. 7B is an example of the frequency spectrum of the received detection signal for a case where the power of the transmission ultrasonic pulse is small (i.e. in the event of the side lobe).

To explain this more in detail, FIG. 7A shows the signal power distribution of the received echo signal when the diffusion distance is at Z0 and Z1 for a case where the power of the transmission ultrasonic pulse is big. As the diffusion distance gets longer (Z1>Z0), the signal power of the harmonics frequency (F1=2F0) gets substantially bigger.

On the other hand, FIG. 7B shows the signal power distribution of the received detection signal when the diffusion distance is at Z0 and Z1 for a case where the power of the transmission ultrasonic pulse is small. In this case, the signal power of the harmonics frequency does not substantially get bigger even if the diffusion distance is longer.

From these remarkable points mentioned above, by considering the power ratios of the fundamental wave frequency component and the harmonics frequency component (harmonics power/fundamental wave power), it is possible to say that the ultrasonic echo that is received from the side lobe direction, which is a cause of the artifact (the virtual image), tends to have a smaller power ratio than the power ratio of the ultrasonic echo that is received from the main lobe direction. Therefore, it is possible to reduce the artifact when the output of the received detection signal is suppressed based on this power ratio.

Figure 8:
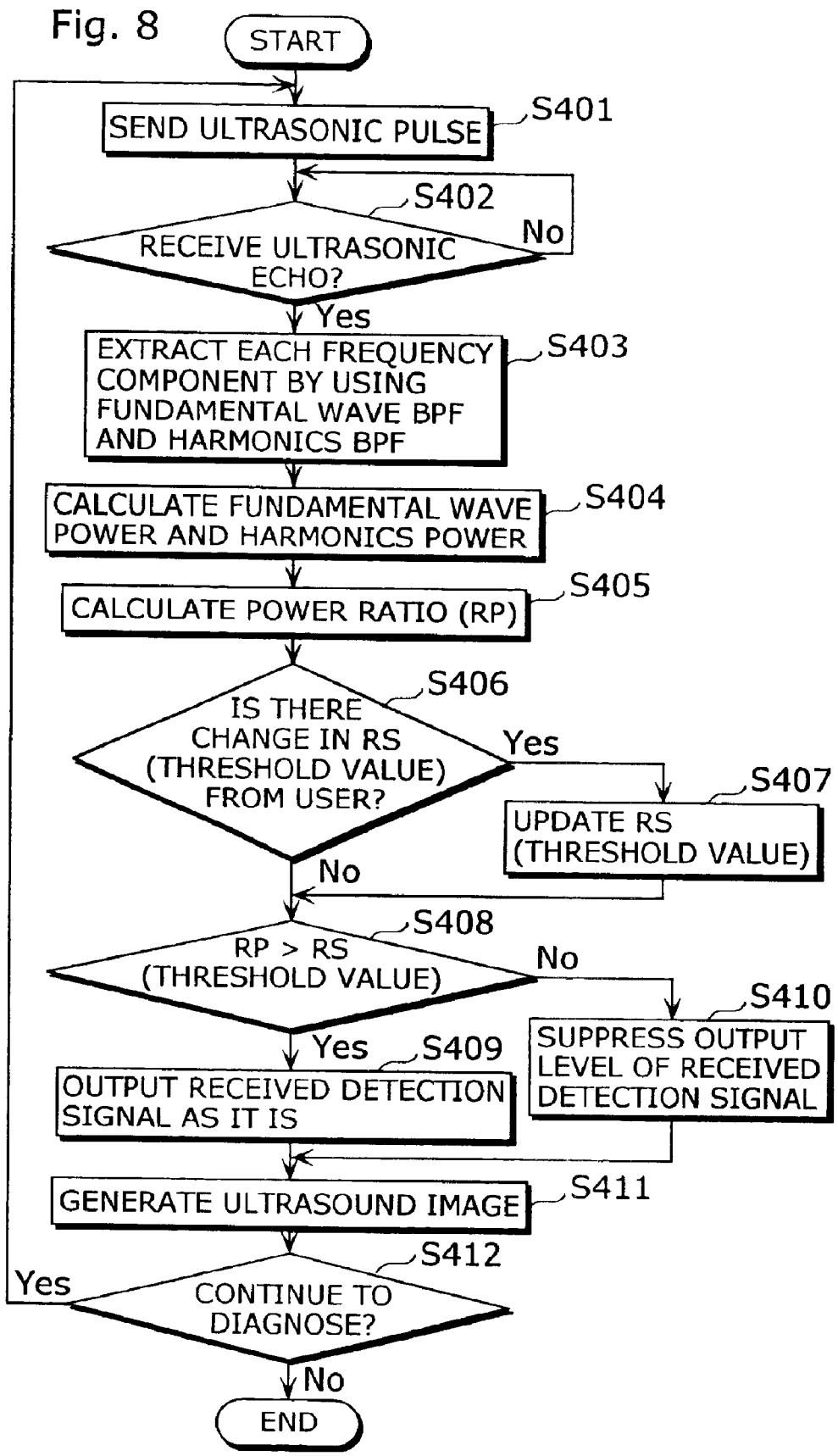
FIG. 8 is a flowchart that shows a flow of processes of the ultrasonic diagnostic apparatus according to the first embodiment.

Next, based on what has been mentioned above, the actions which are taken by the ultrasonic diagnostic apparatus 10 according to the first embodiment will now be described with reference to FIG. 8. FIG. 8 is a flowchart that shows a flow of actions of the ultrasonic diagnostic apparatus 10.

At first, when the ultrasonic pulse is sent to the object (S401), the ultrasonic pulse is reflected at a sound impedance boundary within the object, and the ultrasonic pulse comes back to the search unit 11 with some time delay that occurs according to the reflection depth after transmission has started (S402). This means that the ultrasonic echo which is received by the search unit 11 is received in a way such that reflection waves from the main lobe direction and the side lobe direction are superimposed on each other. The ultrasonic echo which is received by the search unit 11 is converted into the received echo signal and sent to the beam forming and adding unit 14. The beam forming and adding unit 14 corrects the difference in the reaching time that is spent by the received echo signal between oscillators that form the search unit 11, and executes focusing on the received echo signal. Since it is unknown whether the received echo signal after the beam formation and addition is the received echo signal based on the ultrasonic echo that is reflected from the main lobe or the received echo signal based on the ultrasonic echo that is reflected from the side lobe, and since the received echo signal contains noise components, the fundamental wave frequency component is extracted and its signal power is calculated by using the fundamental wave BPF unit 151 and the fundamental wave detecting unit 161 (S403, S404). On the other hand, the harmonics frequency component is extracted and its signal power is calculated by using the harmonics BPF unit 152 and the harmonics detecting unit 162 (S403, S404).

Then, the power ratio calculating unit 17 calculates a ratio Rp of each signal power which is calculated by the fundamental wave detecting unit 161 and the harmonics detecting unit 162 (S405).

Here, when the user changes the above-described power ratio threshold value Rs (S406), the value of the power ratio threshold value Rs that is stored in the power ratio reference memory 18 is updated (S407).

In addition, the power ratio comparing unit 19 compares the power ratio Rp that is calculated by the power ratio calculating unit 17 with the power ratio threshold value Rs that is memorized by each diffusion distance (depth), which is stored in the power ratio reference memory 18, and makes a notification based on its comparison result to the detection signal suppressing unit 110.

If the notification which is received from the power ratio comparing unit 19 shows that "it is an artifact", the detection signal suppressing unit 110 suppresses a signal level of the received detection signal that is output from the fundamental wave detecting unit 161 (S410) (for example, it suppresses it to 20 percent). If not, the detection signal suppressing unit 110 keeps the same signal level of the received detection signal that is output from the fundamental wave detecting unit 161 (S409).

Lastly, the display unit 111 generates an ultrasonic image based the received detection signal that is output from the detection signal suppressing unit 110, and displays the generated ultrasonic image (S411). These processes mentioned above are continued until the diagnosis using the ultrasonic diagnostic apparatus is completed (S401–S412).

In the above explanation, the received detection signal, which is input to the detection signal suppressing unit 110, is regarded as the received echo signal that is output from the fundamental wave detecting unit 161. However, when an ultrasonic image display mode (Tissue Harmonics Imaging Mode) with harmonics is used, the received detection signal that is output from the harmonics detecting unit 162 shall be used as its input.

As has been mentioned above, according to the ultrasonic diagnostic apparatus 10 of the first embodiment, detection and suppression of the received echo signal that is generated by the side lobe, which is a cause of the artifact contained in the ultrasonic echo, are conducted by calculating and comparing the power ratios of "harmonics power/fundamental wave power" in the received detection signal. Therefore, it is possible to generate a clear ultrasonic image, which has fewer artifacts, as the ultrasonic image which is displayed on the display unit 111, and to thereby prevent misdiagnosis.

Second Embodiment

Similar to the ultrasonic diagnostic apparatus 10 according to the first embodiment, an ultrasonic diagnostic apparatus according to the second embodiment is an ultrasonic diagnostic apparatus that can reduce an artifact by suppressing a level of the received detection signal which is generated by the side lobe in the ultrasonic pulse. However, the ultrasonic diagnostic apparatus according to the second embodiment is especially different from the ultrasonic diagnostic apparatus according to the first embodiment in that the ultrasonic diagnostic apparatus of the second embodiment uses a dynamic band pass filter as a band pass filter for extracting a fundamental wave frequency component or a harmonics frequency component.

Figure 9:
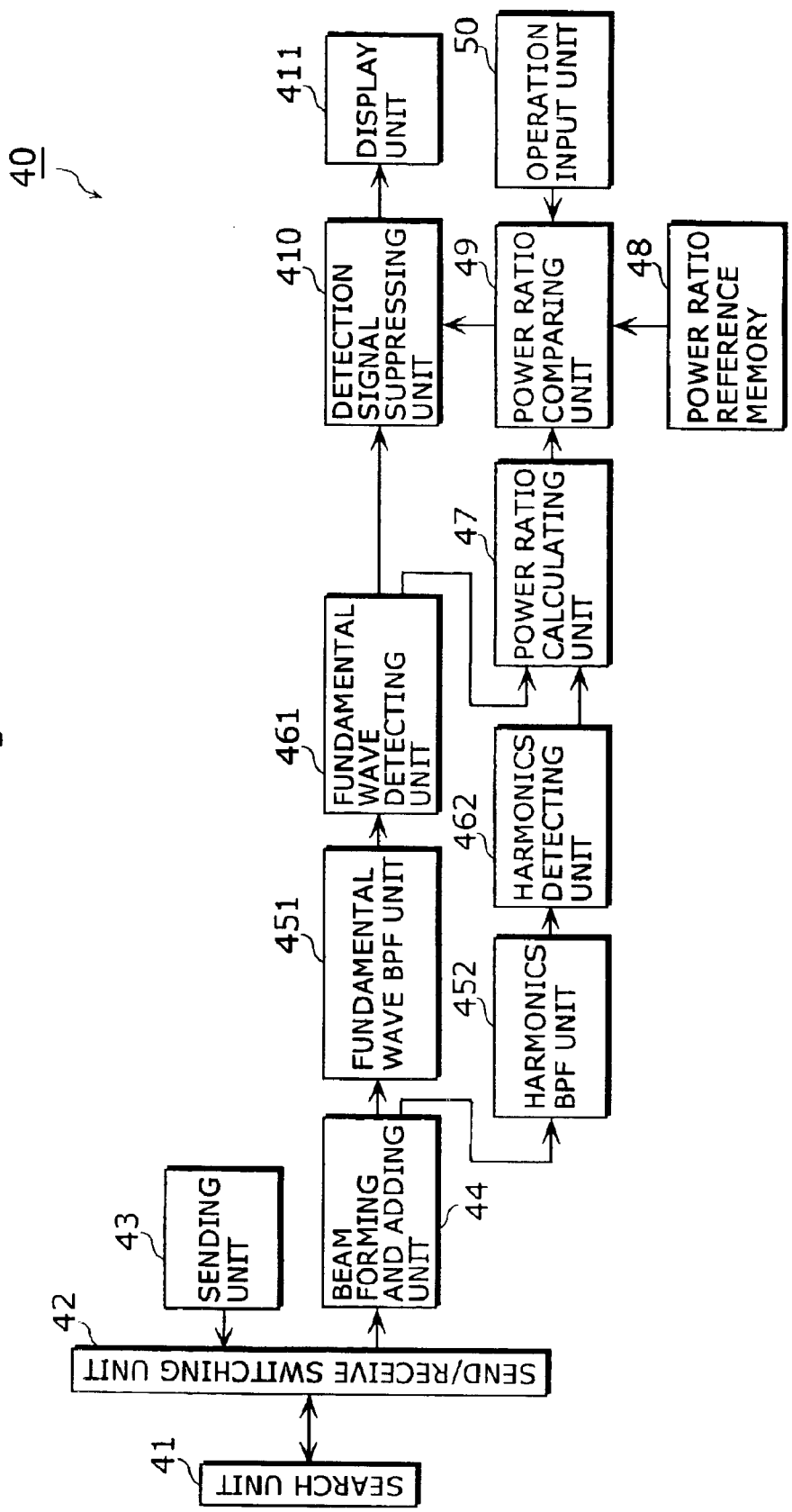
FIG. 9 is a block diagram that shows a functional configuration of the ultrasonic diagnostic apparatus according to a second embodiment of the present invention.

FIG. 9 is a block diagram that shows a functional configuration of an ultrasonic diagnostic apparatus 40 according to the second embodiment. As shown in FIG. 9, the ultrasonic diagnostic apparatus 40 includes the following elements: a search unit 41; a send/receive switching unit 42; a sending unit 43; a beam forming and adding unit 44; a fundamental wave DBPF (a dynamic band pass filter) unit 451; a DBPF (a dynamic band pass filter) unit 452; a fundamental wave detecting unit 461; a harmonics detecting unit 462; a power ratio calculating unit 47; a power ratio reference memory 48; a power ratio comparing unit 49; an operation input unit 50; a detection signal suppressing unit 410; and a display unit 411.

Because the configuration of the ultrasonic diagnostic apparatus according to the second embodiment is almost the same as the ultrasonic diagnostic apparatus of the first embodiment, the following explanation focuses on the components which are different between the first and second embodiments. Because the search unit 41, the send/receive switching unit 42, the sending unit 43, the beam forming and adding unit 44, the fundamental wave detecting unit 461, the harmonics detecting unit 462, the power ratio calculating unit 47, the power ratio reference memory 48, the power ratio comparing unit 49, the detection signal suppressing unit 410 and the display unit 411 in FIG. 9 are the same as the search unit 11, the send/receive switching unit 12, the sending unit 13, the beam forming and adding unit 14, the fundamental wave detecting unit 161, the harmonics detecting unit 162, the power ratio calculating unit 17, the power ratio reference memory 18, the power ratio comparing unit 19, the detection signal suppressing unit 110 and the display unit 111 in the ultrasonic diagnostic apparatus 10 according to the aforementioned first embodiment, respectively, their explanation is omitted here.

Figure 10:
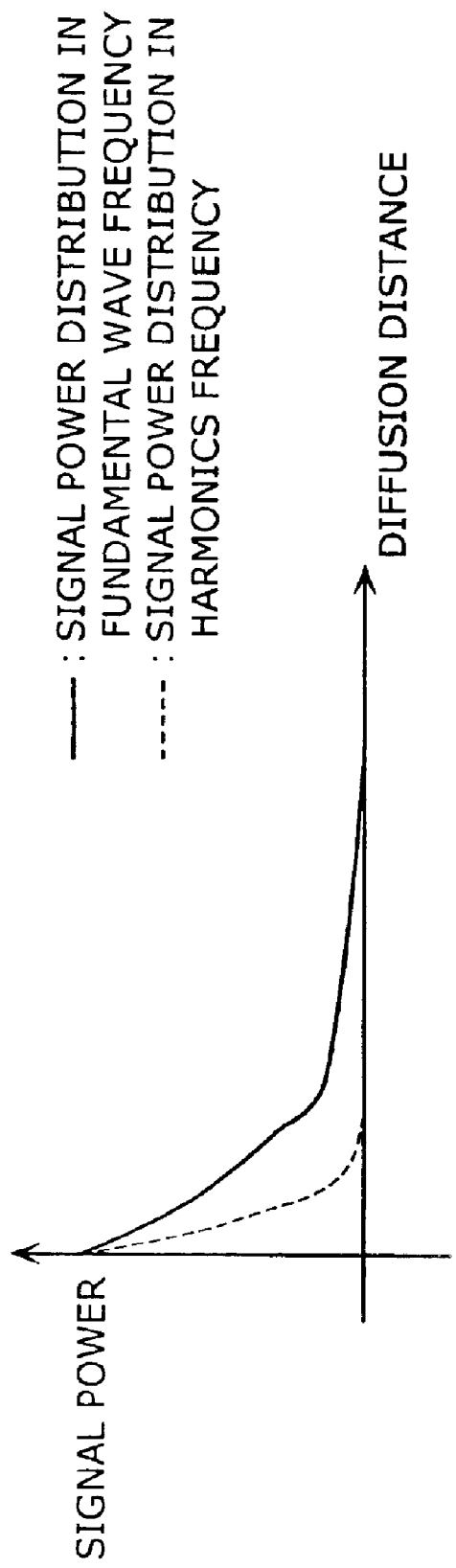
FIG. 10 is an example of a curve showing a relationship between diffusion distance (depth) and the received signal power.
Figure 11:
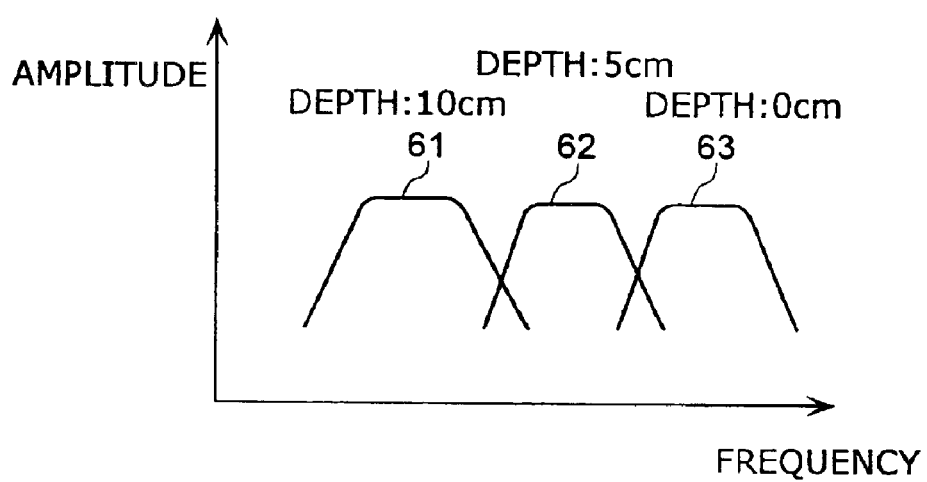
FIG. 11 is an example of a frequency property curve showing a relationship between diffusion distance (depth) and amplitude of the received signal.

The fundamental wave DBPF unit 451 and the harmonics DBPF unit 452 have a filtering feature of which band pass width dynamically moves to a lower frequency bandwidth, as the receiving depth gets deeper. A reason why the BPF having such a feature is used is because it has a characteristic that the signal power is remarkably attenuated as the frequency gets higher, which is shown in FIG. 10, although the power of the transmitted ultrasonic pulse is attenuated according to diffusion distance (depth). FIG. 11 shows an example of the frequency feature of this dynamic band pass filter.

By using the dynamic band pass filter, it becomes possible to control the band pass bandwidth to be changed according to the diffusion distance (depth) in a dynamic way. Therefore, it is possible to obtain the received detection signal in a good S/N ratio, and eventually possible to generate the ultrasonic image that is unlikely to cause misdiagnosis.

Figure 12:
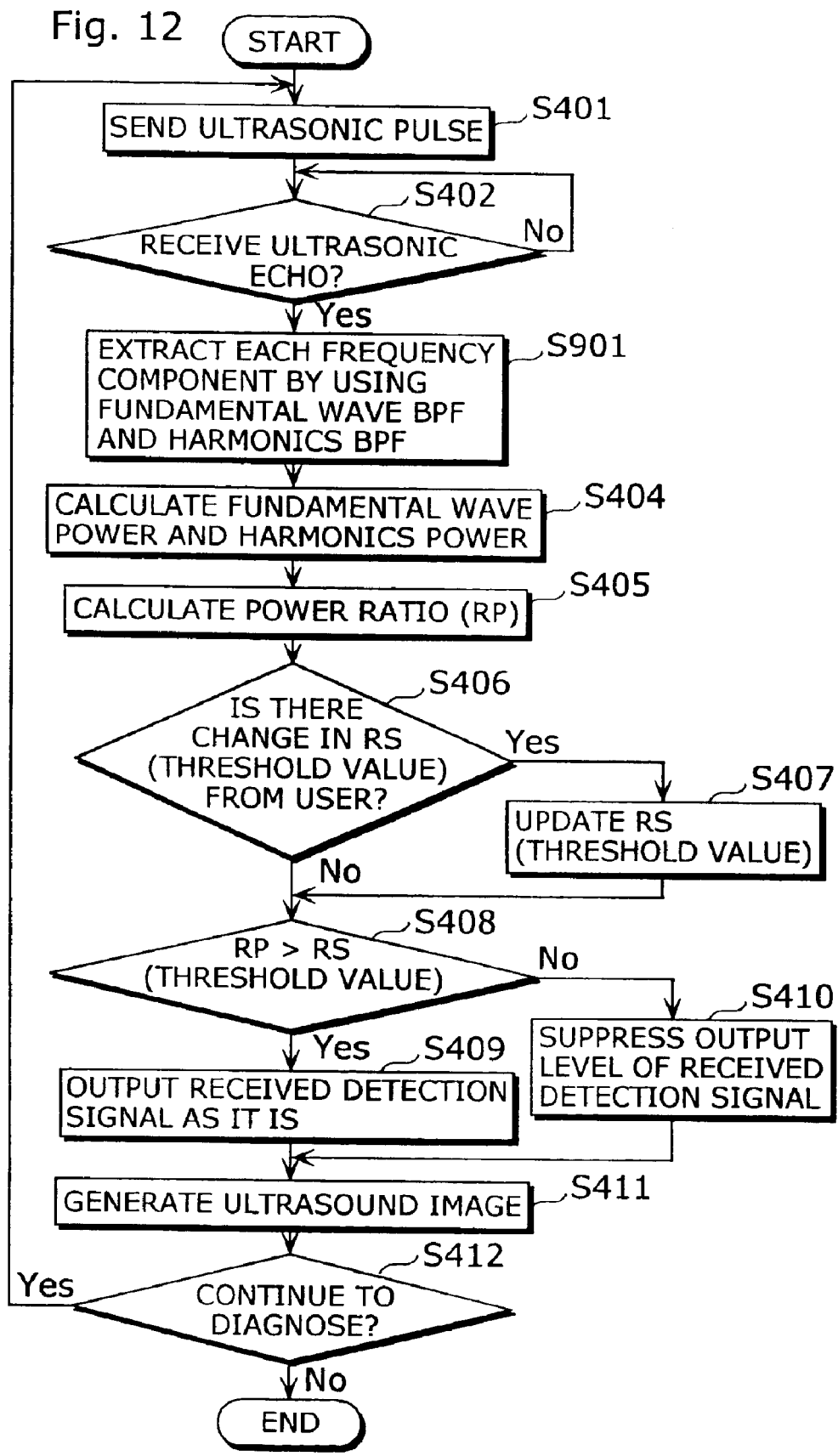
FIG. 12 is a flow chart that shows a flow of processes of the ultrasonic diagnostic apparatus according to the second embodiment.

Based on what has been mentioned above, actions which are taken by the ultrasonic diagnostic apparatus 40 of the second embodiment will now be explained with reference to FIG. 12. FIG. 12 is a flowchart showing a flow of actions of the ultrasonic diagnostic apparatus 40. As clarified in FIG. 12, the flow is the same as the flow in FIG. 8 according to the first embodiment except for the facts that a DBPF is used in the fundamental wave DBPF unit 451 and a DBPF is also used in the harmonics DBPF unit 452 (S901).

In the above explanation, in the same way as the first embodiment, the received detection signal that is input to the detection signal suppressing unit 410 is regarded as the received detection signal which is output from the fundamental wave detection unit 461. However, when the ultrasonic image display mode (the Tissue Harmonics Imaging mode) with the harmonics is used, the received detection signal which is output from the harmonics detecting unit 462 is used as its input.

As mentioned above, according to the ultrasonic diagnostic apparatus 40 of the second embodiment, through calculation and comparison of the power ratios of "harmonics power/fundamental wave power" in the received detection signal, the received echo signal that is generated by the side lobe, which is a cause of an artifact contained in the ultrasonic echo, is detected and suppressed. Additionally, the band pass width is controlled to be changed in a dynamic way according to the diffusion distance (depth), and the artifact is attempted to be reduced by extracting more realistic fundamental wave frequency components and harmonics frequency components. Therefore, it is possible to generate a clearer ultrasonic image as the ultrasonic image which is displayed in the display unit 111, and as a result, misdiagnosis can prevented.

In the first embodiment and the second embodiment mentioned above, the explanation has been provided for a case where the artifact is attempted to be reduced by judging whether or not the echo signal is originated from the side lobe based on the ratio between the signal power of the fundamental wave frequency component and the signal power of the harmonics frequency component. However, the present invention is not limited thereto. For example, based on a ratio between the signal power of the N dimensional harmonics frequency components (N: an integer of 2 or higher) and the signal power of the M dimensional harmonics frequency components (N<M, M: an integer of 3 or higher), the invention may be structured in the same way so as to reduce the artifact by judging whether or not the echo signal is originated from the side lobe.

What is claimed is:

1. An ultrasonic diagnostic apparatus that generates and displays an ultrasonic image of an object to be examined based on a reflection of an ultrasound having a main lobe and a side lobe, said apparatus comprising:

an ultrasonic sending/receiving unit operable to generate the ultrasound, to receive the ultrasound reflected from the object, and to convert the received ultrasound into an electric signal;

a first calculating unit operable to extract an N dimensional harmonics frequency component from the converted electric signal and to calculate a power of the signal of the N dimensional harmonics frequency component, wherein N is an integer greater than or equal to two;

a second calculating unit operable to extract an M dimensional harmonics frequency component from the converted electric signal and to calculate a power of the signal of the M dimensional harmonics frequency component, wherein M is an integer greater than N and greater than or equal to three;

a power ratio calculating unit operable to calculate a power ratio of the calculated power of the signal of the N dimensional harmonics frequency component to the calculated power of the M dimensional harmonics frequency component;

an output controlling unit operable to control and output the electric signal of the N dimensional harmonics frequency component based on a value of the power ratio calculated by said power ration calculating unit; and an image display unit operable to generate and display an ultrasonic image based on the electric signal outputted from said output controlling unit.

2. The ultrasonic diagnostic apparatus according to claim 1, wherein said output controlling unit is operable to compare the power ratio with a specific power ratio threshold value, and to perform the control of the electric signal of the N dimensional harmonics frequency component based on a comparison result of the power ratio with the power ratio threshold value.

3. The ultrasonic diagnostic apparatus according to claim 2, wherein, when the power ratio is equal to or less than the power ratio threshold value, said output controlling unit is operable to decide that the electric signal of the N dimensional harmonics frequency component is an electric signal based on the side lobe, and to suppress and output a signal level of the electric signals.

4. The ultrasonic diagnostic apparatus according to claim 3, further comprising a threshold value updating unit operable to accept an operational input from a user, and to update content of the power ratio threshold value based on the accepted operational input, and wherein said output controlling unit is operable to compare the power ratio with the updated power ratio threshold value.

5. The ultrasonic diagnostic apparatus according to claim 1, wherein said first calculating unit is operable to extract the N dimensional harmonics frequency component by using a first dynamic band filter, and wherein said second calculating unit is operable to extract the M dimensional harmonics frequency component by using a second dynamic band pass filter.

6. An ultrasonic diagnostic apparatus that generates and displays a ultrasonic image of an object to be examined based on a reflection of an ultrasound having a main lobe and a side lobe, said apparatus comprising:

an ultrasound sending/receiving unit operable to generate the ultrasound, to receive the ultrasound reflected from the object, and to convert the received ultrasound into an electric signal;

a first calculating unit operable to extract an N dimensional harmonics frequency component from the converted electric signal and to calculate a power of the signal of the N dimensional harmonics frequency component, wherein N is an integer greater than or equal to two;

a second calculating unit operable to extract an M dimensional harmonics frequency component from the converted electric signal and calculate a power of the signal of the M dimensional harmonics frequency component, wherein M is an integer greater than N and greater than or equal to three;

a power ratio calculating unit operable to calculate a power ratio of the calculated power of the signal of the N dimensional harmonics frequency component to the calculated power of the signal of the M dimensional harmonics frequency component;

an output controlling unit operable to control and output the electric signal of the M dimensional harmonics frequency component based on a value of the power ratio calculated by said power ratio calculating unit; and an image display unit operable to generate and display an ultrasonic image based on the electric signal outputted from said output controlling unit.

7. The ultrasonic diagnostic apparatus according to claim 6, wherein said output controlling unit is operable to compare the power ratio with a specific power ratio threshold value, and to perform the control of the electric signal of the M dimensional harmonics frequency component based on a comparison result of the power ratio with the power ratio threshold value.

8. The ultrasonic diagnostic apparatus according to claim 7, wherein, when the power ratio is equal to or less than the power ratio threshold value, said output controlling unit is operable to decide that the electric signal of the M dimensional harmonics frequency component is an electric signal based on the side lobe, and to suppress and output a signal level of the electric signals.

9. An ultrasonic diagnostic method for generating and displaying an ultrasonic image of an object to be examined based on a reflection of an ultrasound having a main lobe and a side lobe, said method comprising:

generating the ultrasound, receiving the ultrasound reflected from the object, and converting the received ultrasound into an electric signal;

extracting an N dimensional harmonics frequency component from the converted electric signal, and calculating a power of the signal of the N dimensional harmonics frequency component, wherein N is an integer greater than or equal to two;

extracting an M dimensional harmonics frequency component from the converted electric signal, and calculating power of the signal of the M dimensional harmonics frequency component, wherein M is an integer greater than N and greater than or equal to three;

calculating a power ratio of the calculated power of the signal of the N dimensional harmonics frequency component to the calculated power of the signal of the M dimensional harmonics frequency component;

controlling and outputting the electric signal of the N dimensional harmonics frequency component based on a value of the power ratio calculated in said calculating of the power ratio; and generating and displaying an ultrasonic image based on the electric signal outputted in said outputting of the electric signal.

10. The ultrasonic diagnostic method according to claim 9, wherein the power ratio calculated in said calculating of the power ratio is compared with a specific power ratio threshold value, and said controlling and outputting of the electric signal of the N dimensional harmonics frequency component is performed based on a comparison result of the power ratio with the power ratio threshold value.

11. The ultrasonic diagnostic method according to claim 10, wherein, when the power ratio is equal to or less than the power ratio threshold value, the electric signal of the N dimensional harmonics frequency component is decided in said controlling, and outputting of the electric signal of the N dimensional harmonics frequency component to be an electric signal based on the side lobe, and a signal level of the electric signals is suppressed and output.

12. An ultrasonic diagnostic method for generating and displaying an ultrasonic image of an object to be examined based on a reflection of an ultrasound having a main lobe and a side lobe, said method comprising:

generating the ultrasound, receiving the ultrasound reflected from the object, and converting the received ultrasound into an electric signal;

extracting an N dimensional harmonics frequency component from the converted electric signal, and calculating a power of the signal of the N dimensional harmonics frequency component, wherein N is an integer greater than or equal to two;

extracting an M dimensional harmonics frequency component from the converted electric signal, and calculating a power of the signal of the M dimensional harmonics frequency component, wherein M is an integer greater than N and greater than or equal to three;

calculating a power ratio of the calculated power of the signal of the N dimensional harmonics frequency component to the calculated power of the signal of the M dimensional harmonics frequency component;

controlling and outputting the electric signal of the M dimensional harmonics frequency component based on a value of the power ratio calculated in said calculating of the power ratio; and generating and displaying an ultrasonic image based on the electric signal outputted in said outputting of the electric signal.

13. The ultrasonic diagnostic method according to claim 12, wherein the power ratio calculated in said calculating of the power ratio is compared with a specific power ratio threshold value, and said controlling and outputting of the electric signal of the M dimensional harmonics frequency component is performed based on a comparison result of the power ratio with the power ratio threshold value.

14. The ultrasonic diagnostic method according to claim 13, wherein, when the power ratio is equal to or less than the power ratio threshold value, the electric signal of the M dimensional harmonics frequency component is decided in said controlling and outputting of the electric signal of the M dimensional harmonics frequency component to be an electric signal based on the side lobe, and a signal level of the electric signals is suppressed and output.

15. A computer-readable recording medium on which a program for an ultrasonic diagnostic apparatus is recorded, the ultrasonic diagnostic apparatus generating and displaying an ultrasonic image of an object to examined based on a reflection of an ultrasound having a main lobe and a side lobe, wherein said program comprises:

generating the ultrasound, receiving the ultrasound reflected from the object, and converting the received ultrasound into an electric signal;

extracting an N dimensional harmonics frequency component from the converted electric signal, and calculating a power of the signal of the N dimensional harmonics frequency component, wherein N is an integer greater than or equal to two;

extracting an M dimensional harmonics frequency component from the converted electric signal, and calculating a power of the signal of the M dimensional harmonics frequency component, wherein M is an integer greater than N and greater than or equal to three;

calculating a power ratio of the calculated power of the signal of the N dimensional harmonics frequency component to the calculated power of the signal of the M dimensional harmonics frequency component;

controlling and outputting the electric signal of the N dimensional harmonics frequency component based on a value of the power ratio calculated in said calculating of the power ratio; and generating and displaying an ultrasonic image based on the electric signal outputted in said outputting of the electric signal.

16. The program recorded on the computer-readable recording medium according to claim 15, wherein the power ratio calculated in said calculating of the power ratio is compared with a specific power ratio threshold value, and said controlling and outputting of the electric signal of the N dimensional harmonics frequency component is performed based on a comparison result of the power ratio with the power ratio threshold value.

17. The program recorded on the computer-readable recording medium according to claim 16, wherein, when the power ratio is equal to or less than the power ratio threshold value, the electric signal of the N dimensional harmonics frequency component is decided in said controlling and outputting of the electric signal of the N dimensional harmonics frequency component to be an electric signal based on the side lobe, and a signal level of the electric signals is suppressed and output.

18. A computer-readable recording medium on which a program for an ultrasonic diagnostic apparatus is recorded, the ultrasonic diagnostic apparatus generating and displaying an ultrasonic image of an object to be examined based on a reflection of an ultrasound having a main lobe and a side lobe, wherein said program comprises:

generating the ultrasound, receiving the ultrasound reflected from the object, and converting the received ultrasound into an electric signal;

extracting an N dimensional harmonics frequency component from the converted electric signal, and calculating a power of the signal of the N dimensional harmonics frequency component, wherein N is an integer greater than or equal to two;

extracting an M dimensional harmonics frequency component from the converted electric signal, and calculating a power of the signal of the M dimensional harmonics frequency component, wherein M is an integer greater than N and greater than or equal to three;

calculating a power ratio of the calculated power of the signal of the N dimensional harmonics frequency component to the calculated power of the signal of the M dimensional harmonics frequency component;

controlling and outputting the electric signal of the M dimensional harmonics frequency component based on a value of the power ratio calculated in said calculating of the power ratio; and generating and displaying an ultrasonic image based on the electric signal outputted in said outputting of the electric signal.

19. The program recorded on the computer-readable recording medium according to claim 18, wherein the power ratio calculated in said calculating of the power ratio is compared with a specific power ratio threshold value, and said controlling and outputting of the electric signal of the M dimensional harmonics frequency component is performed based on a comparison result of the power ratio with the power ratio threshold value.

20. The program recorded on the computer-readable recording medium according to claim 19, wherein, when the power ratio is equal to or less than the power ratio threshold value, the electric signal of the M dimensional harmonics frequency component is decided in said controlling and outputting of the electric signal of the M dimensional harmonics frequency component to be an electric signal based on the side lobe, and a signal level of the electric signals is suppressed and output.

* * * * *